US008470585B2

(12) United States Patent
De Vocht et al.

(10) Patent No.: US 8,470,585 B2
(45) Date of Patent: *Jun. 25, 2013

(54) PROCESS FOR ADENOVIRUS PURIFICATION FROM HIGH CELL DENSITY CULTURES

(75) Inventors: Marcel Leo De Vocht, Woerden (NL); Marloes Veenstra, Houten (NL)

(73) Assignee: Crucell Holland B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/501,731

(22) PCT Filed: Oct. 14, 2010

(86) PCT No.: PCT/EP2010/065436
§ 371 (c)(1),
(2), (4) Date: Apr. 12, 2012

(87) PCT Pub. No.: WO2011/045381
PCT Pub. Date: Apr. 21, 2011

(65) Prior Publication Data
US 2012/0202268 A1  Aug. 9, 2012

Related U.S. Application Data

(60) Provisional application No. 61/279,060, filed on Oct. 15, 2009.

(30) Foreign Application Priority Data

Oct. 15, 2009  (EP) ..................................... 09173119

(51) Int. Cl.
*C12N 1/02* (2006.01)
*C12N 15/00* (2006.01)
*A61K 39/00* (2006.01)
*A61K 39/23* (2006.01)

(52) U.S. Cl.
USPC ..................... 435/261; 424/184.1; 424/233.1; 435/320.1

(58) Field of Classification Search
None
See application file for complete search history.

(56) References Cited

U.S. PATENT DOCUMENTS

| | | |
|---|---|---|
| 5,559,099 A | 9/1996 | Wickham et al. |
| 5,837,511 A | 11/1998 | Falck-Pedersen et al. |
| 5,846,782 A | 12/1998 | Wickham |
| 5,851,806 A | 12/1998 | Kovesdi |
| 5,891,690 A | 4/1999 | Massie |
| 5,965,541 A | 10/1999 | Wickham |
| 5,981,225 A | 11/1999 | Kochanek et al. |
| 5,994,106 A | 11/1999 | Kovesdi |
| 5,994,128 A | 11/1999 | Fallaux et al. |
| 6,020,191 A | 2/2000 | Scaria et al. |
| 6,040,174 A | 3/2000 | Imler et al. |
| 6,113,913 A | 9/2000 | Brough et al. |
| 6,485,958 B2 | 11/2002 | Blanche |
| 6,492,169 B1 | 12/2002 | Vogels et al. |
| 6,544,424 B1 | 4/2003 | Shevitz |
| 7,326,555 B2 | 2/2008 | Konz, Jr. et al. |
| 2005/0153420 A1* | 7/2005 | Konz, Jr. et al. ............ 435/239 |
| 2010/0098725 A1* | 4/2010 | Liu et al. .................... 424/209.1 |
| 2011/0207202 A1 | 8/2011 | Leitjens et al. |

FOREIGN PATENT DOCUMENTS

| | | |
|---|---|---|
| EP | 1 371 723 | 12/2003 |
| WO | WO 96/26281 | 8/1996 |
| WO | WO 97/00326 | 1/1997 |
| WO | WO 97/08298 | 3/1997 |
| WO | WO 98/22588 | 5/1998 |
| WO | WO 98/39411 | 9/1998 |
| WO | WO 00/03029 | 1/2000 |
| WO | WO 02/44348 | 6/2002 |
| WO | WO 03/097797 | 11/2003 |
| WO | WO 03/104467 | 12/2003 |
| WO | WO 2004/099396 | 11/2004 |
| WO | WO 2005/080556 | 9/2005 |
| WO | WO 2005/095578 | 10/2005 |
| WO | WO2006/052302 | 5/2006 |
| WO | WO 2006/108707 | 10/2006 |
| WO | WO 2008/006494 | 1/2008 |
| WO | WO 2010/060719 | 6/2010 |
| WO | WO 2011/045378 | 4/2011 |

OTHER PUBLICATIONS

Berdichevsky et al., Establishment of Higher Passage PER.C6 Cells for Adenovirus Manufacture; Biotechnol. Prog. 2008, 24, 158-165.
Cortin et al., High-Titer Adenovirus Vector Production in 293S Cell Perfusion Culture; Biotechnol. Prog. 2004, 20, 858-863.
Fallaux et al., Characterization of 911: A New Helper Cell Line for the Titration and Propagation of Early Region 1-Deleted Adenoviral Vectors; Human Gene Therapy 7:215-222; Jan. 20, 1996.
Goerke et al., Development of a Novel Adenovirus Purification Process Utilizing Selective Precipitation of Cellular DNA; published online May 11, 2005 in Wiley InterScience (www.interscience.wiley.com) 10 pages.
International Preliminary Report on Patentability; PCT/EP2010/065436 dated Feb. 28, 2012.
International Search Report; PCT/EP2010/065436 dated Jan. 26, 2011.
Maranga et al., Characterization of Changes in PER.C6™ Cellular Metabolism During Growth and Propagation of a Replication-Deficient Adenovirus Vector; published online Apr. 15, 2005 in Wiley InterScience (www.interscience.wily.com) 11 pages.
Yuk et al., Perfusion Cultures of Human Tumor Cells: A Scalable Production Platform for Oncolytic Adenoviral Vectors; published online Apr. 23, 2004 in Wiley InterScience (www.interscience.wiley.com) 6 pages.

\* cited by examiner

*Primary Examiner* — Benjamin P Blumel
(74) *Attorney, Agent, or Firm* — TraskBritt (57) ABSTRACT

The invention provides methods for large-scale adenovirus purification from high cell density suspensions, using host cell DNA fragmentation and/or precipitation followed by a clarification step with tangential flow filtration.

30 Claims, 2 Drawing Sheets

PROCESS FOR ADENOVIRUS PURIFICATION FROM HIGH CELL DENSITY CULTURES

CROSS-REFERENCE TO RELATED APPLICATION(S)

This is a national phase entry under 35 U.S.C. §371 of international Patent Application PCT/EP2010/065436, filed Oct. 14, 2010, published in English as International Patent Publication WO2011/0453841 A1 on Apr. 21, 2011, which claims the benefit under Article 8 of the Patent Cooperation Treaty and under 35 U.S.C. §119(e) to U.S. patent application Ser. No. 61/279,060 filed on Oct. 15, 2009 and under Article 8 of the Patent Cooperation Treaty to European Patent Application Serial No. 09173119.0 filed Oct. 15, 2009.

The invention relates to the field of virus production. More particularly, it concerns improved methods for the purification of adenovirus particles from a cell suspension.

BACKGROUND OF THE INVENTION

Recent developments in the field of vaccine production have created the need for large scale manufacturing. Robust and high yield processes are needed to support the world with sufficient amounts of (recombinant) vaccines to combat infectious diseases.

Vaccines against infectious diseases can be based on recombinant adenovirus particles. For that reason, great efforts are being put into the optimization of cell based processes for adenovirus production. Cells are being cultured at increasing densities and subsequently infected in order to obtain higher total virus yields. Such high cell density processes are being disclosed in e.g. WO 2010/060719 of Crucell Holland B V, and in Yuk et al. (2004). A process for the production of large concentrations of recombinant adenovirus was described therein. This optimized process relies on the ability to infect cultures at high cell density (e.g. higher than $5\times10^6$ cells/ml) with preservation of a high virus productivity per cell. Herewith, it offers a method to obtain a harvested virus solution with high virus concentration in a single bioreactor. Typical virus particle (VP) yields of said processes are about $1.5$-$2.5\times10^{12}$ VP/mL.

Processes wherein cells are cultured at high densities are prone to the accumulation of high amounts of cell debris and host cell DNA. These contaminants have to be discarded further down the purification process, which is a cumbersome operation. A method for discarding host cell DNA from a harvested cell culture was disclosed previously in U.S. Pat. No. 7,326,555. The method consists of selectively precipitating host cell DNA away from the cell culture. A selective precipitating agent could specifically bind to host cell DNA and leave adenovirus particles unprecipitated. The method in this reference however has only been described for cell cultures with low cell density, wherein cell debris and host cell DNA are present in low quantities.

It was not known hitherto that said process could be applied in a culture containing high cell densities. To the contrary, from the prior art a strong suggestion could be inferred that a precipitating agent as used in said method would not selectively precipitate host cell DNA away from the culture and would precipitate virus particles when used at high concentrations (Goerke et al. 2004).

The adenovirus-containing cell culture harvests are generally further processed in order to obtain purified adenovirus. A clarification step using e.g. depth filtration and/or tangential flow filtration (TFF) is usually included in said purification process. The use of TFF requires a relatively clean harvest, that is, containing limited quantities of cell debris or other impurities such as e.g. host cell DNA. An excess of said impurities could possibly block the filters. As a consequence, clarification by TFF is commonly used further down the purification process e.g. as a third or fourth process step.

Separation of adenovirus from an adenovirus-containing cell suspension directly after harvest, using tangential flow filtration was previously described in e.g. EP1371723. However, the adenovirus was grown on adherent cells, which remained in the bioreactor after harvesting. Therefore, the virus containing suspension that was further processed contained very low concentrations of cell debris and host cell DNA. WO2006/052302 also describes the use of TFF directly after harvest. However, the cell densities of the virus-containing harvest used therein were much lower then $5\times10^6$ cells/ml. As disclosed herein, the use of TFF in the clarification step directly after harvest is not feasible for cell cultures containing high cell densities.

Since cell culture processes are being up-scaled and cells are being cultured at increasing densities, there is a need in the industry for downstream processes that enable the treatment of high cell density suspensions. This applies in particular to the field of adenovirus production.

SUMMARY OF THE INVENTION

The present invention relates to methods of purifying adenovirus particles from a cell lysate from a cell suspension, in particular from a high cell density suspension.

Attempts to purify adenovirus from a high cell density suspension with existing processes resulted in very low virus recovery, as exemplified herein (example 1). The concentrations of impurities in said high cell density suspension obtained after harvest were generally too high to allow for direct adenovirus purification. Down stream processing of high cell density suspensions using known processes would commonly require a multitude of steps. A first filtration step would consist of a rough filtration to remove large precipitates and cell debris. Subsequently, one or two more selective filtration steps would be required to obtain a sufficiently purified adenovirus suspension.

We have surprisingly found and disclose herein that directly subsequent to preparing a cell lysate containing adenovirus, the consecutive use of host cell DNA fragmentation and/or precipitation followed by a clarification step comprising tangential flow filtration (TFF) resulted in a highly purified adenovirus suspension.

Surprisingly, the cell lysate containing adenovirus, large amounts of cell debris, host cell DNA and other impurities could efficiently be processed to purified adenovirus with the the present invention. Herewith, the present invention provides a novel process suited for host cell DNA removal in large scale adenovirus purification processes.

With the incorporating of DNA fragmentation or precipitation into the purification process, a single clarification step was sufficient to purify adenovirus from a high cell density suspension, using TFF for clarification.

The invention provides a method for purifying adenovirus particles from a cell suspension having a cell density ranging from $5\times10^6$ to $150\times10^6$ cells per ml, said method comprising: a) lysing cells within said cell suspension; b) fragmenting and/or precipitating host cell DNA within said cell suspension; and c) subjecting the cell suspension obtained from step b) to a clarification by tangential flow filtration.

In some embodiments said adenovirus is purified from a cell suspension having a cell density ranging from $5\times10^6$ to 150×10⁶ cells per ml, for instance 5×10⁶ to 50×10⁶ cells per ml or 10×10⁶ to 30×10⁶ cells per ml.

In another embodiment said precipitation in step b) is performed by selectively precipitating host cell DNA away from the adenovirus particles by addition of a selective precipitating agent.

In a preferred embodiment, the tangential flow filtration is performed with membrane having a pore size ranging from 0.1 to 0.65 μm.

In other preferred embodiments, the tangential flow filtration is performed with a hollow fiber. In yet another preferred embodiment said tangential flow filtration is performed with an ATF system.

DETAILED DESCRIPTION OF THE INVENTION

The present invention relates to methods of purifying adenovirus particles from a high cell density suspension. According to the invention, the high cell density suspensions are obtained by culturing cells to high cell densities. Such culturing can for instane be performed in batch, fed-batch or perfusion mode. Methods for culturing cells to high cell densities are known to the person skilled in the art. Specific methods for obtaining high cell density cultures are disclosed in e.g. WO2004/099396, WO2005/095578, WO2008/006494, WO 2010/060719.

According to the present invention, a high cell density suspension contains between about $5 \times 10^6$ and $150 \times 10^6$ cells/mL, e.g. between about $8 \times 10^6$ and $120 \times 10^6$ cells/mL, e.g. between about $12 \times 10^6$ and $100 \times 10^6$ cells/mL, e.g. between about $20 \times 10^6$ and $80 \times 10^6$ cells/mL.

In a preferred embodiment of the present invention, the cell density in said high cell density suspension ranges between about $10 \times 10^6$ and $50 \times 10^6$ cells/mL, e.g. at least about $15 \times 10^6$ cells/mL, e.g. at least about $20 \times 10^6$ cells/mL, e.g. at least about $25 \times 10^6$, e.g. up to about $30 \times 10^6$ cells/mL, e.g. up to about $35 \times 10^6$ cells/mL, e.g. up to about $40 \times 10^6$ cells/mL, e.g. up to about $45 \times 10^6$ cells/mL.

According to the invention, high cell density cultures are infected with adenovirus particles in order to allow said adenovirus to propagate in the cell suspension. Herewith, high cell density suspensions are obtained that contain high concentrations of adenovirus, in a single bioreactor. Methods for infecting high cell density cultures are also known to the person skilled in the art. Specific methods for obtaining said high cell density cultures with high virus concentration are disclosed in e.g. EP08168181.9, Cortin et al. 2004 and Yuk et al. 2004. These references describe processes for the production of large quantities of recombinant adenovirus. These processes rely on the ability to infect cultures at high cell density with preservation of a high adenovirus productivity per cell. Herewith, it offers a method to obtain a high cell density suspension with high adenovirus concentrations, in a single bioreactor. Typical yields of current processes e.g. for recombinant adenovirus 35 (rAd35) are about $1.5$-$2.5 \times 10^{12}$ VP/mL. Once the adenovirus has propagated in the cell culture, killing most of the cells, the adenovirus particles are, according to the present invention, purified from the high cell density suspension.

The method of the present invention as a first step includes lysing the cells contained in the high cell density suspension. Lysing high cell density suspensions, which were infected with adenovirus particles, cause large quantities of cell debris and host cell DNA to accumulate in the cell suspension. These accumulations render subsequent down stream processing of the cell suspension cumbersome.

The present invention provides a method suited for purifying adenovirus particles from the cell lysate of high cell density suspensions. Large quantities of host cell DNA can selectively be precipitated away from the adenovirus particles within the high cell density suspension by adding a selective precipitating agent to the cell lysate such that at least about 80% of host cell DNA molecules are precipitated away from the high cell density suspension containing the adenovirus particles. As disclosed herein, the precipitation step allows for the precipitation of contaminating host cell DNA, with at least a 80% reduction in host cell DNA, preferably 90% and even more preferably, as exemplified herein, about a 95% reduction in host cell DNA following clarification with TFF.

Lysis

The first step of the process includes lysing the cells within the cell suspension. This first step, wherein the cell membranes are lysed, allows for the harvest of both cell-associated (intracellular) and non-associated (extracellular) adenovirus from the infected high cell density suspension. Host cell detergent lysis, while being the preferred method of lysing virus containing host cells, can be replaced by non-mechanical lysis methods (such as enzyme treatment) and/or mechanical shear methods (such as hollow fiber ultrafiltration) to release maximum amounts of adenovirus. Methods that can be used for active cell lysis are known to the person skilled in the art, and have for instance been discussed in WO 98/22588, p. 28-35. Useful methods in this respect are for example, freeze-thaw, solid shear, hypertonic and/or hypotonic lysis, liquid shear, sonication, high pressure extrusion, detergent lysis, combinations of the above, and the like. In one embodiment of the invention, the cells are lysed using at least one detergent. Use of a detergent for lysis has the advantage that it is an easy method, and that it is easily scalable.

Detergents that can be used, and the way they are employed, are generally known to the person skilled in the art. Several examples are for instance discussed in WO 98/22588, p. 29-33. Detergents, as used herein, can include but are not limited to anionic, cationic, zwitterionic, and nonionic detergents. Examples of detergents are for instance Triton and/or Polysorbate-80. In one embodiment, the detergent used is Triton X-100. In addition, a solvent such as TNBP can be added to the lysate or clarified lysate at low concentration to complement these detergents in their ability to inactivate enveloped viruses. Also, autolysis of the infected host cells by the adenovirus therein may provide for substantial release of intracellular adenovirus and may be used in the processes of the invention. Therefore, any form of host cell lysis which is known in the art may be used to liberate intracellular virus into the host cell culture medium for eventual harvesting by the methods disclosed herein. It is clear to the person skilled in the art that the optimal concentration of the detergent may vary, for instance within the range of about 0.1%-1% (w/w).

Fragmentation and Selective Precipitation

Following lysis, host cell DNA can be fragmented or precipitated away from the virus containing cell suspension.

In a preferred embodiment, host cell DNA is precipitated by addition of a selective precipitating agent (SPA) solution.

This step allows for the selective precipitation of host cell DNA while leaving the virus particles unmodified in the liquid phase. As exemplified herein, this early stage precipitation step results in about at least 90% reduction in host cell DNA following clarification.

The SPAs which may be useful in practicing the present invention include, but are not limited to, amine copolymers, quaternary ammonium compounds, and any respective mixtures thereof. More specifically, the many forms of polyethylene (PEI) are very efficient in neutralization of excess anionic charge (DNA impurities). A list of possible SPAs that can be used appropriately in the present invention is given in U.S. Pat. No. 7,326,555 (column 12, lines 56-67 and column 13, lines 1-28), incorporated by reference herein. Appropriate SPAs for use in the present invention include but are not limited to the following classes and examples of commercially available products: monoalkyltrimethyl ammonium salts (examples of commercially available products include cetyltrimethylammonium bromide or chloride as CTAB, tetradecyltrimethylammonium bromide or chloride (TTA), alkyltrimethyl ammonium chloride, alkylaryltrimethyl ammonium chloride, dodecyltrimethylammonium bromide or chloride, dodecyldimethyl-2-phenoxyethylammonium bromide, hexadecylamine: chloride or bromide salt, dodecyl amine or chloride salt, and cetyldimethylethyl ammonium bromide or chloride), monoalkyldimethylbenzyl ammonium salts (examples include alkyldimethylbenzyl ammonium chlorides and benzethonium chloride as BTC), dialkyldimethyl ammonium salts (commercial products include domiphen bromide (DB), didecyldimethyl ammonium halides, and octyldodecyldimethyl ammonium chloride or bromide), heteroaromatic ammonium salts (commercial products include cetylpyridium halides (CPC or bromide salt and hexadecylpyridinium bromide or chloride), cis-isomer 1-[3-chloroallyl]-3,5,7-triaza-1-azoniaadamantane, alkyl-isoquinolinium bromide, and alkyldimethylnaphthyl-methyl ammonium chloride (BTC 1110). Polysubstituted quaternary ammonium salts, (commercially available products include, but are not limited to alkyldimethylbenzyl ammonium saccharinate and alkyldimethylethylbenzyl ammonium cyclohexylsulfamate), bis-quaternary ammonium salts (product examples include 1,10-bis(2-methyl-4-aminoquinolinium chloride)-decane, 1,6-bis{1-methyl-3-(2,2,6-trimethyl cyclohexyl)-propyldimethyl ammonium chloride] hexane or triclobisonium chloride, and the bis-quat referred to as CDQ by Buckman Brochures), and polymeric quaternary ammonium salts (includes polyionenes such as poly[oxyethylene (dimethyliminio)ethylene(dimethyliminio)ethylene dichloride], poly[N-3-dimethylammonio)propyl]N-[3-ethyleneoxyethylenedimethylammonio)propyl]urea dichloride, and alpha-4-[1-tris(2-hydroxyethyle)ammonium chloride). As the skilled man will understand from U.S. Pat. No. 7,326,555, wherein several of these were shown to work and wherein it was shown that the skilled person can routinely find the appropriate concentrations for these compounds to selectively precipitate DNA, these are examples of SPAs, and based on the disclosure therein and the disclosure of the instant invention it is clear that these will also be suitable in the present invention.

In a preferred embodiment, cationic detergents are used in the present invention. In an even more preferred embodiment, dialkyldimethylammonium salts such as domiphen bromide (DB) are used in the present invention. Though a large number of potential SPAs can be used to practice the present invention, domiphen bromide is of particular interest due primarily to its availability as a GMP grade raw material and current use in other products intended for human use. More specifically, since domiphen bromide is extensively used as an active ingredient in oral hygiene products as well as topical antibiotic cremes, this molecule is produced in large quantities and released under cGMP conditions.

The optimal SPA concentration that is used in high cell density suspensions for precipitating host cell DNA away from the cell suspension was determined herein. Although it was anticipated, based on the prior art, that adenovirus particles would immediately precipitate when being put in contact with high concentrations of SPA, unexpectedly, the adenovirus particles remained unprecipitated. Indeed, it was shown in the prior art, for instance in U.S. Pat. No. 7,326,555, that in low cell density suspensions (up to $1\times10^6$ cells/ml), adenovirus particles precipitate when the concentration of cationic detergent is increased.

The suspension as produced by lysing high cell density cultures as disclosed herein will contain vastly increased amounts of host cell DNA and other impurities and will therefore need increased quantities of cationic detergent (e.g. increased by a factor 2). It was thus expected, based on extrapolation of the results at low cell density, that this increase in cationic detergent concentration would lead to precipitation of the totality of the adenovirus particles present in the suspension.

However, surprisingly, at high SPA concentrations, the selective removal of contaminating host cell DNA from a high cell density suspension containing virus particles was still possible. In a preferred embodiment of the present invention, the SPA, preferably DB, is added to a concentration ranging from 1.2 to 5 mM. In an even more preferred embodiment the SPA, preferably DB, is added to a concentration ranging from 1.3 to 2.2 mM, e.g. 1.4 to 2 mM, e.g. 1.4 to 1.8 mM, e.g. 1.5 to 1.6 mM. Based on the present disclosure, it is clear that the skilled man in the art knows how to determine appropriate SPA concentration windows for a given cell density at harvest.

The appropriate concentration of DB for treating an adenovirus containing high cell density suspension comprising a cell density ranging between $10\times10^6$ and $150\times10^6$ cells/mL ranges between about 1.2 mM and 5 mM. The appropriate concentration of DB for treating an adenovirus containing high cell density suspension comprising a cell density ranging between $10\times10^6$ and $50\times10^6$ cells/mL ranges between about 1.3 mM and 2.2 mM. The appropriate concentration of DB for treating an adenovirus containing high cell density suspension harvest comprising a cell density ranging between $10\times10^6$ and $30\times10^6$ cells/mL ranges between about 1.3 and 2 mM, e.g. between about 1.4 and 1.9 mM, e.g. between about 1.4 and 1.8 mM, e.g. between about 1.4 and 1.7 mM, e.g. between about 1.45 and 1.65 mM, e.g. about 1.5-1.55 mM.

It will be within the purview of the skilled man in the art to test potential substitutes for the SPAs disclosed herein to identify a compound which effectively precipitates nucleic acid molecules and other cellular debris away from adenovirus particles as exemplified herein for domiphen bromide (DB). Therefore, this present invention relates in part to methods of purifying adenovirus particles from a high cell density suspension. Said methods comprise selectively precipitating host cell nucleic acid molecules away from the adenovirus particles within the post-lysis high cell density suspension by adding a selective precipitation agent to the post-lysis host cell culture medium.

Although the preferred method for removing host cell DNA from the cell suspension is selecive precipitation, the invention is not limited thereto. Any other method of removing host cell DNA is also included in the present invention.

Therefore, in one embodiment, host cell DNA is fragmented, that is: cut into pieces. According to the present invention, fragmentation of host cell DNA following lysis can be performed by adding a nuclease into the cell suspension. Exemplary nucleases suitable for use in the present invention include Benzonase®, Pulmozyme®, or any other DNase and/or RNase commonly used withing the art. In preferred embodiments of the invention, the nuclease is Benzonase®, which rapidly hydrolyzes nucleic acids by hydrolyzing internal phosphodiester bonds between specific nucleotides, thereby reducing the viscosity of the cell lysate. Benzonase® can be commercially obtained, e.g. from Merck KGaA (code W214950).

The concentration of nuclease that is needed for adequate fragmentation depends on i.e. the host cell density, the temperature and the time of reaction. The person skilled in the art knows how to determine and optimize the required concentration of nuclease for a succesfull fragmentation of the host cell DNA.

Clarification

The SPA-treated cell lysate obtained from the previous steps is subsequently clarified to remove precipitated host cell DNA, cell debris and other impurities.

Attempts to directly purify adenovirus from a high cell density suspension with a one stage clarification process, resulted in low virus recovery, as exemplified herein (example 1). The concentrations of impurities in said high cell density suspension obtained after harvest were generally too high to allow for direct virus purification. Normally, combinations of at least two consecutive filters, as often used and recommended in the art and as exemplified herein, are necessary for appropriate clarification.

We have surprisingly found and disclose herein that combining DNA precipitation with a clarification step using TFF allows for virus purification from a high cell density suspension with high recovery. A single tangential flow filtration step was sufficient to remove cell debris and nucleic acid precipitates from the virus-containing suspension. The host cell DNA was precipitated for over 95% and the virus recovery was higher than 80%. Hence, according to the present invention, it is possible to use TFF as a single clarification step. The clarified virus-containing suspension obtained with the method of the present invention is substantially reduced in host cell DNA and other impurities compared to the original lysate (obtained in step a) of the present method).

According to the present invention, the filters used in a TFF set up are for example hollow fiber filters from GE Healthcare or JM separations; other alternatives are flat screen filters from Millipore or Sartorius stedim biotech. In said TFF set up, the virus particles are collected in the permeate while cell debris, precipitated host cell DNA and other impurities remain in the retentate. It was shown herein that hollow fiber filters were very appropriate for processing high cell density suspensions. Therefore, in a preferred embodiment of the present invention, the TFF is performed with a hollow fiber filter.

According to the present invention, the pore size of said filters is preferably ranging from 0.1 to 1 µm. In a preferred embodiment of the present invention the pore size is ranging from 0.2 to 0.65 µm. Said pore sizes allow for virus particles to pass the membrane and for cell debris, precipitated host cell DNA and other impurities to be retained by the filter. The filter modules are preferably prewetted with water following the manufacturer's instructions. The liquid is recirculating through the modules using tubing and a peristaltic pump.

In certain embodiments of the present invention TFF is used in the form of alternating tangential filtration (ATF). ATF is a form of tangential flow filtration and it was found herein that clarification using ATF was particulary well suited for virus recovery from suspensions with high concentrations of cell debris, host cell DNA and other impurities. Tangential flow can be achieved according to methods known to the person skilled in the art and as described e.g. in U.S. Pat. No. 6,544,424. The advantage of using an ATF system (e.g. ATF System, Refine Technology, Co., East Hanover, N.J.) is that the feed and retentate streams change directions with every ATF pump cycle (cycle consist of a pressurization and exhaust mode). This creates a reverse flow sweeping action and a continually changing trans membrane pressure (TMP) across the membrane. During exhaust a vacuum is created during which some material is back-flushed from the permeate side to the retentate side, resulting in cleaning of the membrane. The use of the ATF will result in less fouling of the membrane resulting in a higher virus recovery yield. The person skilled in the art can determine the optimal ATF and permeate flow rates for maximum yield. According to the present invention, the filters used in said ATF system are for example hollow fiber filters from GE healthcare.

An additional advantage of using an ATF system is that the set up that is used for clarification can be used earlier for culturing cells in perfusion mode. Indeed, a bioreactor connected to an ATF system can be used in the first place to culture cells to high cell densities. Very high cell densities of over $100 \times 10^6$ viable cells/mL can be obtained with the use of an ATF perfusion system, e.g. with PER.C6 cells (see e.g. Yallop et al, 2005 and WO 2005/095578). Once the cells have reached a high cell density, they can be infected in order to obtain a highly concentrated virus-containing cell suspension. The ATF system which remains connected to the bioreactor throughout the process could subsequently be used to purify the virus from said high cell density suspension.

The combination of selective precipitation with clarification by TFF removes at least 70%, preferably at least 80% and even more preferably at least 90% of the host cell DNA contained in the high cell density lysate obtained after harvest.

Methods of Further Purification

In certain embodiments, the harvested virus particles are further purified. Further purification of the virus can be performed in several steps comprising concentration, ultrafiltration, diafiltration or separation with chromatography as described in for instance WO 2005080556, incorporated herein by reference. Other steps, such as, anion exchange membrane chromatography, sterile filtration, reversed-phase adsorption, hydroxyapatite chromatography can also be used. These steps are for example disclosed in U.S. Pat. No. 7,326,555, incorporated in its entirety by reference herein. The person skilled in the art knows how to find the optimal conditions for each purification step. Also WO 98/22588, incorporated in its entirety by reference herein, describes methods for the production and purification of virus particles.

In certain embodiments according to the invention, the clarified adenovirus particle suspension can be treated by ultrafiltration. Ultrafiltration is used to concentrate the virus suspension. The suspension can be concentrated 5 to 20 times and possibly be treated with nuclease (as mentioned hereabove). Another aspect of the invention is the subsequent introduction of an exchange buffer via diafiltration. Diafiltration, or buffer exchange, using ultrafilters is a way for removal and exchange of salts, sugars and the like. The person skilled in the art knows under which conditions the buffer exchange shoud take place and which buffers are appropriate for this step.

The particular ultrafiltration membrane selected will be of a size sufficiently small to retain adenovirus particles but large enough to effectively clear impurities. Depending on the manufacturer and membrane type, nominal molecular weight cutoffs between 10 and 1000 kDa may be appropriate. Ultrafiltration using tangential flow mode is preferred. In said mode, the step may be controlled by setting a fixed cross-flow with or without backpressure on the retentate return, setting a fixed transmembrane pressure, or fixing both the cross-flow and the permeate flux.

According to the invention, a following step can be an anion exchange chromatography step. During said step adenovirus particles are bound to a positively charged material, e.g. a membrane, cartridge or column. Subsequent elution allows for separating the virus particles from impurities and remaining host cell DNA.

For adenovirus purification with a Mustang Q membrane absorber, the NaCl concentration for loading and washing could presumably be anywhere from 0.3 to 0.4 M at pH 7.5 and would shift at alternating pH's. More preferably the NaCl concentration is 0.35 M. The pH of the buffers needs to be high enough for adenovirus to bind (greater than approximately 6.5). In addition, the pH of the buffer system should also be low enough to avoid viral instability. The precise maximum pH which is usable will depend on the specific stability profile of the adenovirus and the buffer components, and can easily be determined by the skilled man in the art for that particular application. As a guide and certainly not a limitation, the pH could potentially range from about 5-10.

The presence of 0.1% PS-80 in the buffers is highly preferred to achieving low residual DNA levels in the product because it attenuates adenovirus/DNA association and adenovirus aggregation. It will be within the realm of routine experimentation for the person skilled in the art to establish higher or lower detergent concentrations or alternative detergents which would be useful to promote dissociation of adenovirus particles away from other adenovirus as well as various cell contaminants. It is also within this same realm of experimentation that the person skilled in the art may choose an alternative detergent to the process buffer. Examples for such alternative detergents can be found in U.S. Pat. No. 7,326,555. Anion exchange membrane chromatography products such as those produced by Pall (e.g. Mustang™ series) and Sartorius (e.g. Sartobind series) are suitable for virus purification according to the present invention. U.S. Pat. No. 6,485,958 or WO 05/080556 describe the use of anion exchange chromatography for purification of recombinant adenovirus.

The binding capacity for virus on a membrane absorber such as Mustang Q (Pall Corporation) is extremely high, and in the order of $7 \times 10^{13}$ VP/ml. Other membrane absorbers and resins that are suitable for adenovirus purification in this process include but are in no way limited to Source 15Q and Source 30Q (GE life sciences), Q-Sepharose XL (GE life sciences), Fractogel TMAE (EM industries), Sartobind Q (Sartorius), Adsept Q (Natrix separations), CIM QA (BIA separations). Adenovirus elution would preferably be performed using a buffer containing NaCl. The skilled person knows how to optimize the NaCl concentration.

In certain embodiments, it is preferred to use at least one anion exchange chromatography step. After the anion exchange chromatography step, the adenovirus may be sufficiently pure. In certain embodiments however a size exclusion chromatography step is further performed to increase the robustness of the process. This step may be prior to or after the anion exchange chromatography step. Obviously, other purification steps may also be suitably combined with an anion exchange chromatography step. The use of anion exchange chromatography for adenovirus purification has been extensively described, and this aspect is therefore well within the reach of the person skilled in the art. Many different chromatography matrices have been employed for purification of adenovirus and are suitable, and the person skilled in the art can easily find the optimal anion exchange material for purifying the adenovirus.

In any particular embodiment of the present invention, the anion exchange product can be diafiltered into formulation buffer and sterile filtered. Alternatively, an additional chromatography step (e.g. cation exchange) may be added either before or after the diafiltration with the potential to improve the robustness of impurity and/or virus/prion clearance.

An additional ultrafiltration step could also be possible at this stage. Tangential flow ultrafiltration is useful in removing residual protein and nucleic acid and to exchange the adenovirus into a formulation buffer. The choice between 300 kDa and 500 kDa membranes is dictated by the tradeoffs between yield and improved impurity clearance. Other membrane configurations (such as a hollow fiber) are acceptable substitutes. The selected ultrafiltration membrane will be of a size sufficiently small to retain adenovirus particles but large enough to effectively clear impurities. Depending on the manufacturer and membrane type, nomimal molecular weight cutoffs between 100 and 1000 kDa may be appropriate.

A sterile filtration step may be included in the process, which is helpful in eliminating bioburden. The product can be filtered through a 0.22 micron modified polyvinylidene fluoride (PVDF) membrane (e.g. Millipore, Millipak).

Optional downstream processing steps could be added in the process. These could e.g. include a size exclusion chromatography step, a reversed-phase adsorption step and/or a hydroxyapathite chromatography step. More details on each of these steps can be found in e.g. U.S. Pat. No. 7,326,555, WO 03/097797, WO 02/44348.

International application WO 97/08298 describes the purification of adenoviruses using certain chromatographic matrices to prevent damage to the viruses, including anion exchange and size exclusion steps.

Certain ultrafiltration methods are also very suitable for purification of adenovirus, as disclosed in WO 2006/108707. Such steps may be performed in addition to or instead of certain chromatographic purification steps.

Scale of Cell Culture Systems and Down Stream Processing Systems

The processes of the present invention are scalable. The cell cultures used in the present invention range from small scale cultures (e.g. 1-10 liter runs) to medium scale cutures (e.g. 20 -1000 L runs) up to large commercial scale preparations, such as 1000 to 50 000 L production runs. The initial process steps (lysis, depth filtration and ultrafiltration) scale with culture volume while the anion exchange chromatography and subsequent steps scale with adenoviral particle input. Therefore, the size of the latter steps will be based on a bioreactor productivity estimate of at least $1 \times 10^{12}$ adenovirus particles per mL (vp/mL). These high adenovirus yields can for instance be obtained by infecting high cell density cultures (as described e.g. in EP08168181.9). The further purification of these high density cell suspensions containing high concentrations of adenovirus particles is made possible with the present invention. The possibility to process these suspensions, which contain high amounts of cell debris and host cell DNA allow for the purification of high quantities of adenovirus particles per volume of suspension. It is the merit of this invention to provide for a method for processing cell culture batches with high cell densities, containing high concentrations of adenovirus particles and therewith allowing for very high virus yields per processed volume. The present method, although it is applicable to large scale cell cultures will allow for cells to be cultured at smaller scale, yet to higher cell densities and still reach high adenovirus yields which can efficiently be further processed. This method offers the possibility to process highly concentrated adenovirus batches which will have a great impact on the entire adenovirus purification industry.

Adenovirus and Producer Cells

The invention relates to purification of adenovirus. An adenovirus according to this invention can be any wild type, modified, mutated adenovirus and/or recombinant adenoviral vector. Of specific interest in gene vaccination and/or gene therapy applications is the use of a $1^{st}$ or $2^{nd}$ generation replication incompetent adenovirus, crippled by E1 or further deletions, including "gutless" adenovirus vectors. The adenovirus genome is generally associated with benign pathologies in humans. The genome is amenable to manipulation, depending on the strategy utilized to construct the respective vector. A replication-incompetent virus, such as an recombinant adenovirus 35 (rAd35) or 26 (rAd26) vector (as exemplified herein) requires a producer cell line which complements the deletions.

A producer cell (sometimes also referred to in the art and herein as 'packaging cell' or 'complementing cell' or 'host cell') can be any producer cell wherein a desired adenovirus can be propagated. For example, the propagation of recombinant adenovirus vectors is done in producer cells that complement deficiencies in the adenovirus. Such producer cells preferably have in their genome at least an adenovirus E1 sequence, and thereby are capable of complementing recombinant adenoviruses with a deletion in the E1 region. Further the adenovirus may have a deletion in the E3 region, which is dispensable from the Ad genome, and hence such a deletion does not have to be complemented. Any E1-complementing producer cell can be used, such as human retina cells immortalized by E1, e.g. 911 or PER.C6 cells (see U.S. Pat. No. 5,994,128), E1-transformed amniocytes (See EP patent 1230354), E1-transformed A549 cells (see e.g. WO 98/39411, U.S. Pat. No. 5,891,690), GH329:HeLa (Gao et al, 2000, Human Gene Therapy 11: 213-219), 293, and the like. In certain embodiments, the producer cells are for instance HEK293 cells, or PER.C6 cells, or 911 cells, or IT293SF cells, and the like. Preferably PER.C6 cells (ECACC deposit no. 96022940, deposited on 29 February 1996 at the ECACC, CAMR, Porton Down, Salisbury SP4 0JG, United Kingdom; see U.S. Pat. No. 5,994,128), or cells derived therefrom are used as producer cells.

The replication-deficient adenoviral vector can be generated by using any species, strain, subtype, or mixture of species, strains, or subtypes, of an adenovirus or a chimeric adenovirus as the source of vector DNA (see for instance WO 96/26281, WO 00/03029), which for instance may provide the adenoviral vector with the capability of infecting certain desired cell types. In a preferred embodiment of the present invention, rAd35 or rAd26 is used as an adenovirus.

The person skilled in the art will be aware of the possibilities to propagate adenoviral vectors of different serotypes on specific host cells, using methods such as for instance disclosed in U.S. Pat. No. 6,492,169 or in WO 03/104467, and references therein. For instance, for propagation of E1-deficient rAd35, specific producer cells that express E1B-55K of Ad35 can be constructed, for instance based on existing producer cells that express E1A and E1B of Ad5 such as PER.C6 or HEK293 cells (see, e.g. U.S. Pat. No. 6,492,169), as is known to the skilled person. Alternatively and preferably, existing (Ad5-) complementing cell lines such as for instance PER.C6 or HEK293 can be used without modification of the cells for propagation of E1-deficient rAd35 or rAd26, by inclusion of the E4-orf6 coding sequence of Ad5 into the rAd35 or rAd26 vector, as extensively disclosed in for instance WO 03/104467, incorporated in its entirety by reference herein. Thus, propagation of adenoviral vectors of any serotype can be done on producer cells using means and methods well known to the person skilled in the art. Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913, and Thomas Shenk, "Adenoviridae and their Replication", M. S. Horwitz, "Adenoviruses", Chapters 67 and 68, respectively, in Virology, B. N. Fields et al., eds., 3d ed., Raven Press, Ltd., New York (1996), and other references mentioned herein. The invention is further explained in the following examples. The examples do not limit the invention in any way. They merely serve to clarify the invention.

EXAMPLES

Example 1

Direct TFF Clarification does not Work for High Cell Density Harvests

PER.C6 cells were grown in a bioreactor at 37° C. and infected with Ad35 in serum-free culture medium for 3 days. Cells were harvested at a cell density between 20 and $30 \times 10^6$ cells/ml and virus titers of 1 to $1.5 \times 10^{12}$ VP/ml. Viruses were released from the cells upon the addition of the nonionic detergents Triton X-100 and Tween-80 to final concentrations of respectively 0.1 and 0.05%. Lysis time was between 2 and 24 hrs. Subsequent to lysis, the virus-containing harvest was clarified by tangential flow filtration (TFF).

The clarification was performed using either a 0.2 µm (GE Healthcare, model CFP-2-E-4MA, 0.042 m²) or a 0.65 µm (GE Healthcare, model CFP-6-D-4MA, 0.046 m²) hollow fiber filter. One liter of lysed harvest was concentrated by at least a factor of 3. Following the clarification a flush was perfomed using three times the retentate volume, in a bleed and feed operation. Filtration experiments were performed at a permeate flux ranging between 15 and 40 LMH. The virus recovery over the clarification step was determined in the following table.

TABLE 1

| | Process parameters | | | Performance parameters | | | | |
|---|---|---|---|---|---|---|---|---|
| Exp. # | Pore size (µm) | Cell density (x$10^6$ cells/ml) | Virus titer (x$10^{11}$ VP/ml) | HC-DNA precipitated (%) | HC-DNA (ng/1 x $10^{11}$ vp) | Virus recovery ppt (%) | Virus recovery clarificat. (%) | Overall virus recovery (%) |
| 1 | 0.2 | 29.2 | 11.4 | not performed | not performed | not performed | 0 | 0 |
| 2 | 0.65 | 20.1 | 15 | not performed | not performed | not performed | 0 | 0 |

There was no virus recovery after clarification. This was somewhat unexpected, since for instance EP1371723 and WO2006/052302 described the use of TFF for clarification of adenovirus harvests successfully. Apparently, the high cell densities of the current process impede this step and render the TFF unsuitable for direct clarification.

Example 2

Selective Host Cell DNA Precipitation in High Cell Dnsity Sspensions ective host cell DNA precipitation was demonstrated in the prior art (Goerke et al (2005), U.S. Pat. No.7,326,555) for cell densities up to 1×$10^6$ cells/ml. It was shown therein that (at low cell densities) at least 80% of the host cell DNA was precipitated away from the cell suspension with a 90% recovery of virus particles. However, it was hitherto completely unknown if such selective precipitation would be feasible at high cell density, since such cell suspensions would contain much higher amounts of host cell DNA and cell debris, and therefore it would be expected that much higher amounts of DNA precipitating agent would be required, whereas extrapolation of the data from the prior art would suggest that such higher concentrations of DNA precipitating agent would also precipitate the adenovirus.

In order to explore the possibility of DNA precipitation at high cell densities, host cell DNA precipitation was tested in small scale test tubes containing cell densities up to 30×$10^6$ cells/ml. The small scale test tube model was used as a quick screening tool to test whether selective DNA precipitation still occurs at high cell densities.

PER.C6 cells were grown in a bioreactor and infected with Adenovirus 35 (Ad35) and grown at 37° C. in serum-free culture medium for 3 days. Cells were harvested at a cell density between 2 and 30×$10^6$ cells/ml and virus titers ranging from 8×$10^m$ to 1.5×$10^{12}$ VP/ml. Cell lysis was performed over a period of 2 to 24 hours (hrs), by adding the nonionic detergents Triton X-100 and Tween-80 to final concentrations of 0.1% and 0.05% respectively. Incrementing concentrations of Domiphen Bromide (DB) in 40 mM NaCl were added to 3.5 ml of lysed harvest, followed by immediate vortexing for 1 minute. The precipitated material was removed with 0.45 µm polyvinylidene fluoride (PVDF) syringe filters. The filtrates were analyzed for Ad35 and host cell DNA concentrations using a HPLC-AEX and Q-PCR assay respectively.

Figure 1:
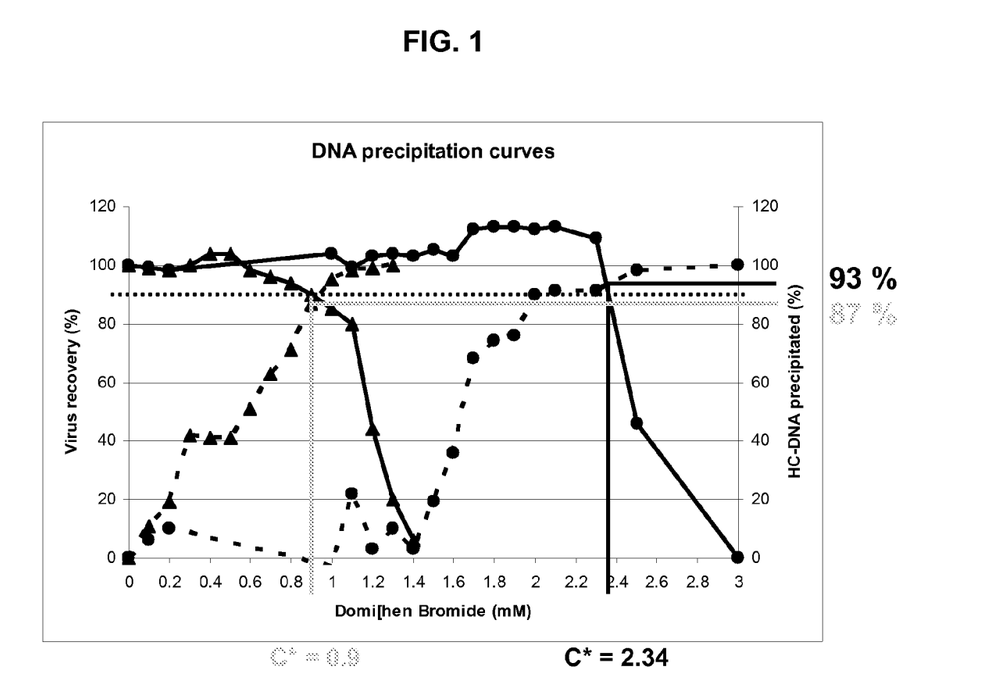
FIG. 1. Adenovirus recovery and precipitated host cell DNA, plotted against the domiphen bromide concentration in low ($2.5 \times 10^6$-$3.5 \times 10^6$ vc/ml) and high ($20 \times 10^6$-$30 \times 10^6$ vc/ml) density cell suspensions.

FIG. 1 shows the virus recovery and precipitated host cell DNA, plotted against the Domiphen Bromide concentration. The curves depicted in triangles are obtained from cell culture harvests having cell densities ranging between 2.5×$10^6$ and 3.5×$10^6$ cells/ml. The curves depicted in circles are obtained from cell culture harvests having cell densities ranging between 20×$10^6$ and 30×$10^6$ cells/ml. The C* (Domiphen Bromide concentration which shows 90% virus recovery) at low and high cell densities and the related percentage of precipitated host cell DNA are highlighted on the graphs.

The DB concentration that is required to precipitate more then 90% of the host cell DNA at cell densities ranging between 20×$10^6$ and 30×$10^6$ cells/ml is increased by a factor of at least 2.5 times compared to the DB concentration required at cell densities that are 10 times lower. Surprisingly, the increased DB concentration did not precipitate the virus particles, as would be expected from extrapolation of the curves obtained at lower cell density.

Figure 2:
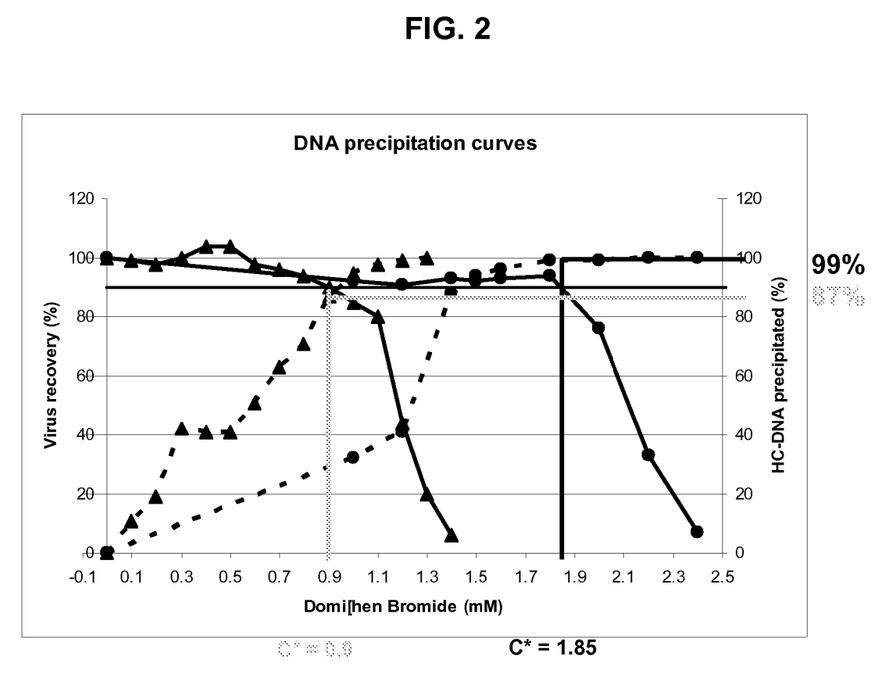
FIG. 2. Adenovirus recovery and precipitated host cell DNA, plotted against the domiphen bromide concentration in low ($2.5 \times 10^6$-$3.5 \times 10^6$ vc/ml) and high ($18 \times 10^6$-$25 \times 10^6$ vc/ml) density cell suspensions.

The experiment was repeated with cell culture harvests having cell densities ranging between 18×$10^6$ and 25×$10^6$ cells/ml. FIG. 2 shows the virus recovery and precipitated host cell DNA, plotted against the Domiphen Bromide concentration. The curves depicted in triangles are obtained from cell culture harvests having cell densities ranging between 2.5×$10^6$ and 3.5×$10^6$ cells/ml. The curves depicted in circles are obtained from cell culture harvests having cell densities ranging between 18×$10^6$ and 25×$10^6$ cells/ml. The C* (Domiphen Bromide concentration which gives 90% virus recovery) at low and high cell densities and the related percentage of precipitated host cell DNA are highlighted on the graphs.

As can be noted from the graphs in FIGS. 1 and 2, the DB concentration which gives 90% virus recovery (C*) for high cell density suspensions may slightly differ between individual experiments, and this is part of the normal variation. However, the graphs consistently demonstrate that a selective prepipitation of DNA is possible also at high cell densities, and that the suitable concentration of SPA (here DB) is significantly higher than for the low cell density cultures, but much lower than would be expected based on extrapolation. Thus, the skilled person will recognize that there is a range rather than a fixed point of suitable concentrations for the selective precipitating agent, and based upon the disclosure herein can find the suitable range. For instance, appropriate concentrations of DB for treating an adenovirus containing high cell density suspension harvest comprising a cell density ranging between about 10×$10^6$ and 30×$10^6$ cells/mL range between about 1.3 and 2 mM.

Based on these results, the person skilled in the art will now be aware that DNA precipitation can be extrapolated to adenovirus containing suspensions containing even higher cell densities, e.g. of about 40×$10^6$ cells/mL, e.g. of about 50×$10^6$ cells/mL, e.g. up to about 100×$10^6$ cells/mL, e.g. up to about 150×$10^6$ cells/mL, and that adenovirus from such high cell density suspensions can be purified with the process from the present invention.

Thus, it is possible according to the present invention to use selective DNA precipitation in the purification of adenovirus particles from high cell density suspensions.

Example 3

Selective Host Cell DNA Precipitation in High Cell Density Suspensions at Larger Scale DNA precipitation was tested at scales ranging between 0.5 L and 20 L. The DB concentrations used for DNA precipitation were based on the previous experimental results (FIG. 2). About 80% of the C* concentration as determined in the small scale test tube model was used.

In perfusion mode, the perfusion which was performed with an ATF system, was started 4 days post inoculation at a cell density of approximately $2.5 \times 10^6$ total cells/mL. After 14 days of perfusion the cell suspension was diluted with fresh serum free medium in the bioreactor to a cell density of about $13 \times 10^6$ cells/mL. Subsequently the bioreactor was infected with Ad35 virus. The ATF system was started 5 hours post infection at a medium refreshment rate of 2 vessel volumes per day. After 3 days (post infection) the cells were harvested. The cell density at harvest (CDAH) is given in Table 2.

Subsequent to harvest, cells were lysed over a period of 2 to 24 hours by adding the nonionic detergents Triton X-100 and Tween-80 to final concentrations of respectively 0.1 and 0.05%. Domiphen Bromide was added to the lysed harvest to final concentrations of 0.72 and 1.52 mM in 40 mM NaCl. The precipitated lysate was clarified using two consecutive charged depth filters with different pore sizes. The estimated pore sizes of both filters were ranging between ~10- ~5 µm (Millistak+CE20) and ~1- ~0.2 µm (Cuno Zeta plus 50CP) respectively. The first filter was used to remove large cell debris and impurities. After said pre-filtration, the second filter was used to remove the remaining impurities and precipitated DNA from the virus-containing suspension. The clarification was performed at a constant flux of 100 LMH (liter per square meter per hour) until the pressure reached 5 psi.

Table 2 shows the process parameters and results of the purification process. Lysis, DNA precipitation (DNA ptt) and clarification were performed using 8 different harvests, which differed in volume, cell density at harvest (CDAH) and virus titer. The harvests were taken from 2 L or 10 L bioreactors. The percentage of precipitated host cell DNA (HC-DNA) and the virus recovery over the precipitation step were determined.

TABLE 2

| | Process parameters | | | Results | | |
|---|---|---|---|---|---|---|
| | | | | DNA ppt | Clarification | |
| Exp. # | CDAH ($\times 10^6$ cells/ml) | Virus titer ($\times 10^{11}$ VP/ml) | DB (mM) | Step recovery (%) | Step recovery (%) | HC-DNA reduction (%) |
| 1 | 1.36 | 2.13 | 0.72 | 92 | 86 | 99.6 |
| 2 | 2.47 | 2.24 | | 91 | 86 | 99.9 |
| 3 | 2.37 | 1.85 | | 90 | 90 | 99.2 |
| 4 | 9.1 | 6.7 | 1.52 | 69 | 97 | 99.9 |
| 5 | 18.6 | 8.9 | | 88 | 98 | 99.8 |
| 6 | 20.1 | 15 | | 90 | 82 | 98.3 |
| 7 | 16.7 | 11 | | 99 | 71 | 99.9 |
| 8 | 25.8 | 15.9 | | 104 | 92 | 99.8 |

It is concluded that selective host cell DNA precipitation is possible at high cell density. Indeed, although the DB concentration was increased (with a factor 2), the virus particles remained unprecipitated (see recovery higher than 70%) and the HC-DNA reduction was higher than 98%.

This process offers a method of discarding host cell DNA from the harvest of high cell density cultures without compromising virus recovery. Herewith it allows for the processing of large volumes of high cell density suspensions, which is needed in industrial processes.

It must be noted that for practical reasons, a single DB concentration (1.52 mM) has been used for selective DNA precipitation in experiments 4-8. Said experiments show that adenovirus containing suspensions having a broad range ($9.1 \times 10^6$-$25.8 \times 10^6$ vc/ml) of cell densities can be treated with 1.52 mM of DB. This is consistent with the notion above that the relationship between suitable concentrations of selective precipitating agent and cell density is not a very fixed one, but rather provides for variation so that a range of concentrations of precipitating agent is suitable for a given cell density.

The appropriate concentration of DB for treating an adenovirus containing high cell density suspension comprising a cell density ranging between $10 \times 10^6$ and $50 \times 10^6$ cells/mL ranges between about 1.3 mM and 2.2 mM. The appropriate concentration of DB for treating an adenovirus containing high cell density suspension harvest comprising a cell density ranging between $10 \times 10^6$ and $30 \times 10^6$ cells/mL ranges between about 1.3 and 2 mM.

It is noted that for some experiments at high cell densities (experiments #6 and 7), reduced virus recovery and filter capacity over the $2^{nd}$ filter, as compared to low cell density harvests, were observed. Besides, the use of two consecutive distinct filters renders the process labor intensive and costly.

Example 4

Single Step Clarification of High Cell Density Adenovirus Preparations by Selective Host Cell DNA Precipitation Followed by TFF PER.C6 cells were grown in a perfusion bioreactor and infected with Ad35 and grown at 36° C. in serum-free culture medium for 3 days. Cells were harvested at a cell density between 20 and $30 \times 10^6$ cells/ml and virus titers of 1 to 1.5x $10^{12}$ VP/ml. Viruses were released from the cells upon the addition of the nonionic detergents Triton X-100 and Tween-80 to final concentrations of respectively 0.1 and 0.05%. Lysis time was between 2 and 24 hrs. Subsequent to cell lysis, a DNA precipitation step was performed followed by clarification.

The DNA precipitation was performed using 0.063% to 0.077% of Domiphen Bromide (DB) in 40 mM NaCl. DNA precipitation was performed for 3 hrs with a 2 hrs addition time of DB at an agitation speed of 0.17 to 1.52 m/s$^{-1}$. The clarification was performed using tangential flow filtration with a 0.65 µm (GE Healthcare, model CFP-6-D-4MA, 0.046 m²) hollow fiber filter. One liter of lysed and DNA precipitated harvest was concentrated by at least a factor of 3. Following the clarification a flush was perfomed using three times the retentate volume, in a bleed and feed operation. Filtration experiments were performed at a permeate flux ranging between 15 and 40 LMH. Lysis followed by DNA precipitation and clarification were performed using 3 different harvests. The percentage of precipitated host cell DNA, host cell DNA concentration per $1 \times 10^{11}$ virus partices and the virus recovery after selective precipitation and clarification were determined in table 3.

TABLE 3

| | Process parameters | | Performance parameters | | | | |
|---|---|---|---|---|---|---|---|
| Exp. # | Cell density ($\times 10^6$ cells/ml) | Virus titer ($\times 10^{11}$ VP/ml) | HC-DNA precipitated (%) | HC-DNA (ng/1 $\times 10^{11}$ vp) | Virus recovery ppt (%) | Virus recovery clarificat. (%) | Overall virus recovery (%) |
| 1 | 20.1 | 14.1 | 100 | 8.6 | 88 | 99 | 87 |
| 2 | 17.9 | 17.4 | 99.9 | 6.9 | 110 | 74 | 81.4 |
| 3 | 23.5 | 15.3 | 99.9 | 23.8 | 100 | 81.2 | 81.2 |

Similar to the previous example, it was unexpectedly shown herein that selective DNA precipitation was possible at high cell density. Indeed, although the DB concentration was increased, the virus particles remained unprecipitated (see recovery higher then 80%) and the HC-DNA reduction was higher then 99%.

Despite the failure in example 1, it is shown in this example that tangential flow filtration, when used in combination with selective HC-DNA precipitation allowed for high cell density suspensions to be clarified.

The use of tangential flow filtration instead of a set of two distinct depth filters (as exemplified previously) offers the possibility to process a high cell density suspension to a clarified adenovirus suspension in a single filtration step.

The combination of selective HC-DNA precipitation with the use of tangential flow filtration allows for the removal of host cell DNA from the harvest of high cell density suspension, and unexpectedly does so without compromising adenovirus recovery. In fact, overall adenovirus recovery using this process may even be higher than using classical two-step clarification filtration processes using depth filters. In addition, it renders the purification process less labor intensive and costly, as compared to the process with depth filters. Herewith it allows for the processing of large volumes of high cell density suspensions, which is needed in industrial processes.

REFERENCES

Cortin V, Thibault J, Jacob D, Garnier A. High-Titer Adenovirus Vector Production in 293S Cell Perfusion Culture. Biotechnol. Prog. 2004.

Goerke A, To B, Lee A, Sagar S, Konz K. Development of a Novel Adenovirus Purification Process Utilizing Selective Precipitation of Cellular DNA. Biotechnology and bioengineering, Vol. 91, No. 1, July 5, 2005.

Yuk I H Y, Olsen M M, Geyer S, Forestell SP. Perfusion Cultures of Human Tumor Cells: A Scalable Production Platform for Oncolytic Adenoviral Vectors. Biotechnol. Bioengin. 86: 637-641 (2004).

The invention claimed is:

1. A method for purifying adenovirus particles from a host cell suspension having a cell density between $5\times10^6$ and $150\times10^6$ cells/mL, wherein the method comprises:
   (a) infecting a host cell suspension having a cell density between $5\times10^6$ and $150\times10^6$ cells/mL, and culturing the host cells;
   (b) lysing with a detergent, cells within the host cell suspension having a cell density between $5\times10^6$ and $150\times10^6$ cells/mL; then
   (c) selectively precipitating host cell DNA within the lysed suspension by adding a selective precipitation agent to the lysed suspension, wherein the selective precipitation agent is selected from the group consisting of quaternary ammonium compounds, amine copolymers and mixtures thereof; and then
   (d) subjecting the suspension of step (c) to tangential flow filtration, to obtain a purified adenovirus suspension, wherein steps (b), (c) and (d) are performed consecutively.

2. The method according to claim 1, wherein the selective precipitating agent is domiphen bromide (DB).

3. The method according to claim 2, wherein the domiphen bromide (DB) is added to a final concentration that is between 1.3 and 5 mM.

4. The method according to claim 2, wherein the cell density of the cell suspension is between about $10\times10^6$ and $30\times10^6$ cells/mL, and the DB is added to a final concentration that is between 1.3 and 2 mM.

5. The method according to claim 1, wherein the tangential flow filtration is performed with a membrane having a pore size between 0.1 and 0.65 μm.

6. The method according to claim 1, wherein the tangential flow filtration is performed with a hollow fiber.

7. The method according to claim 1, wherein the tangential flow filtration is performed with an ATF system.

8. The method according to claim 1, wherein at least 80% of the host cell DNA has been removed in the purified adenovirus suspension.

9. The method according to claim 1, wherein the purified adenovirus suspension comprises at least about 80% of the adenovirus particles from the cell suspension.

10. The method according to claim 9, wherein the tangential flow filtration is performed with a membrane having a pore size between 0.1 and 0.65 μm.

11. The method according to claim 9, wherein the tangential flow filtration is performed with a hollow fiber.

12. The method according to claim 9, wherein the tangential flow filtration is performed with an ATF system.

13. The method according to claim 9, wherein at least 80% of the host cell DNA has been removed in the purified adenovirus suspension.

14. The method according to claim 2, wherein the tangential flow filtration is performed with a membrane having a size between 0.1 and 0.65 μm.

15. The method according to claim 2, wherein the tangential flow filtration is performed with a hollow fiber.

16. The method according to claim 2, wherein the tangential flow filtration is performed with an ATF system.

17. The method according to claim 2, wherein at least 80% of the host cell DNA has been removed in the purified adenovirus suspension.

18. The method according to claim 3, wherein the tangential flow filtration is performed with a membrane having a pore size between 0.1 and 0.65 μm.

19. The method according to claim 3, wherein the tangential flow filtration is performed with a hollow fiber.

20. The method according to claim 3, wherein the tangential flow filtration is performed with an ATF system.

21. A method for purifying adenovirus particles from a host cell suspension having a cell density between $5\times10^6$ and $150\times10^6$ cells/mL, wherein the method comprises:
(a) infecting a host cell suspension having a cell density between $5\times10^6$ and $150\times10^6$ cells/mL, and culturing the host cells;
(b) lysing with a detergent, cells within the host cell suspension having a cell density between $5\times10^6$ and $150\times10^6$ cells/mL;
(c) fragmenting host cell DNA within the lysed suspension by adding a nuclease; and
(d) subjecting the suspension of step (c) to tangential flow filtration, to obtain a purified adenovirus suspension, wherein steps (b), (c), and (d) are performed consecutively.

22. The method according to claim 21, wherein the nuclease is a genetically engineered endonuclease from *Serratia marcescens*.

23. The method according to claim 21, wherein the cell density of the cell suspension is between about $10\times10^6$ and $30\times10^6$ cells/mL.

24. The method according to claim 21, wherein the tangential flow filtration is performed with a membrane having a pore size between 0.1 and 0.65 μm.

25. The method according to claim 21, wherein the tangential flow filtration is performed with a hollow fiber.

26. The method according to claim 21, wherein the tangential flow filtration is performed with an ATF system.

27. The method according to claim 21, wherein at least 80% of the host cell DNA has been removed in the purified adenovirus suspension.

28. The method according to claim 21, wherein the purified adenovirus suspension comprises at least about 80% of the adenovirus particles from the cell suspension.

29. A method for purifying adenovirus particles from a host cell suspension having a cell density between $5\times10^6$ and $150\times10^6$ cells/mL, wherein the method comprises the steps of:
(a) infecting a host cell suspension having a cell density between $5\times10^6$ and $150\times10^6$ cells/mL, and culturing the host cells;
(b) lysing with a detergent, the cells within the host cell suspension having a cell density between $5\times10^6$ and $150\times10^6$ cells/mL, to produce a suspension comprising adenovirus particles, host cell DNA, and host cell debris;
(c) selectively precipitating host cell DNA away from the adenovirus particles by adding to the lysed suspension of step (b) at least one selective precipitation agent selected from the group consisting of quaternary ammonium compounds and amine copolymers, to produce a suspension comprising adenovirus particles, precipitated host cell DNA, and host cell debris; and
(d) subjecting the suspension of step (c) comprising adenovirus particles, precipitated host cell DNA, and host cell debris to tangential flow filtration, to obtain a purified adenovirus suspension,
wherein at least 80% of the host cell DNA is removed from the purified adenovirus suspension by steps (b)-(d).

30. A method for purifying adenovirus particles from a host cell suspension having a cell density between about $5\times10^6$ and $150\times10^6$ cells/mL, wherein the method comprises:
(a) infecting a host cell suspension having a cell density between about $5\times10^6$ and $150\times10^6$ cells/mL, and culturing the host cells;
(b) removing at least 80% of host cell DNA from the host cell suspension having a cell density between about $5\times10^6$ and $150\times10^6$ cells/mL, by a selective host cell DNA precipitation step consisting essentially of lysing with a detergent the cells within the host cell suspension, selectively precipitating host cell DNA away from the adenovirus particles by adding at least one selective precipitation agent selected from the group consisting of quaternary ammonium compounds and amine copolymers, and subjecting the suspension to tangential flow filtration.

* * * * *